(12) United States Patent
Wuister

(10) Patent No.: US 8,357,536 B2
(45) Date of Patent: Jan. 22, 2013

(54) INSPECTION METHOD AND APPARATUS

(75) Inventor: Sander Frederik Wuister, Eindhoven (NL)

(73) Assignee: ASML Netherlands B.V., Veldhoven (NL)

( * ) Notice: Subject to any disclaimer, the term of this patent is extended or adjusted under 35 U.S.C. 154(b) by 148 days.

(21) Appl. No.: 12/955,550

(22) Filed: Nov. 29, 2010

(65) Prior Publication Data

US 2011/0129930 A1    Jun. 2, 2011

Related U.S. Application Data

(60) Provisional application No. 61/265,094, filed on Nov. 30, 2009.

(51) Int. Cl.
*G01N 31/22* (2006.01)
*G01N 33/44* (2006.01)
*G01N 21/64* (2006.01)

(52) U.S. Cl. .............. 436/5; 436/85; 436/164; 436/166; 436/172

(58) Field of Classification Search ................ 436/5, 85, 436/164, 166, 172
See application file for complete search history.

(56) References Cited

U.S. PATENT DOCUMENTS

| | | | | |
|---|---|---|---|---|
| 2,920,203 | A * | 1/1960 | Switzer et al. | 250/302 |
| 2,959,471 | A * | 11/1960 | Morgia | 436/5 |
| 3,490,873 | A * | 1/1970 | Corl | 436/5 |
| 3,672,842 | A * | 6/1972 | Florin | 436/164 |
| 3,764,265 | A * | 10/1973 | Mlot-Fijalkowski | 73/104 |
| 4,323,785 | A * | 4/1982 | McComb et al. | 250/473.1 |
| 4,444,701 | A * | 4/1984 | Meguiar | 264/40.1 |
| 4,552,847 | A * | 11/1985 | Bauman | 436/5 |
| 4,599,241 | A * | 7/1986 | Nakaboh et al. | 438/16 |
| 4,731,155 | A | 3/1988 | Napoli | |
| 4,774,188 | A * | 9/1988 | Chandross | 436/5 |
| 5,772,905 | A | 6/1998 | Chou | |
| 5,928,948 | A * | 7/1999 | Malchesky | 436/2 |
| 5,965,446 | A * | 10/1999 | Ishikawa | 436/5 |
| 6,334,960 | B1 | 1/2002 | Willson | |
| 6,607,918 | B2 * | 8/2003 | LaGraff et al. | 436/73 |
| 2004/0124566 | A1 | 7/2004 | Sreenivasan | |
| 2005/0274693 | A1 | 12/2005 | Heidari | |

FOREIGN PATENT DOCUMENTS

WO   WO 02/067055   8/2002

OTHER PUBLICATIONS

Haisma, et al., "Mold-assisted nanolithography: A process for reliable pattern replication", J. Vac. Sci. Technol. B, vol. 14(6), Nov./Dec. 1996, pp. 4124-4128.
Weiss, Shimon, "Fluorescence Spectroscopy of Single Biomolecules", Science, vol. 283, Mar. 12, 1999, pp. 1676-1683.

* cited by examiner

*Primary Examiner* — Arlen Soderquist
(74) *Attorney, Agent, or Firm* — Pillsbury Winthrop Shaw Pittman LLP

(57) ABSTRACT

In an embodiment, there is disclosed an inspection method for detecting the presence of imprintable medium on an imprint lithography template. The method includes contacting the imprint lithography template with a marker, the marker being attachable to imprintable medium that may be on the imprint lithography template, the marker being configured to interact with incident radiation when attached to the imprintable medium, directing radiation at the imprint lithography template, and measuring radiation re-directed by the imprint lithography template to attempt to detect presence of a marker that has attached to the imprintable medium, from the interaction of the marker with the incident radiation, and thus detect the presence of imprintable medium to which the marker is attached.

20 Claims, 5 Drawing Sheets

INSPECTION METHOD AND APPARATUS

This application claims priority and benefit under 35 U.S.C. §119(e) to U.S. Provisional Patent Application No. 61/265,094, entitled "Inspection Method and Apparatus", filed on Nov. 30, 2009. The content of that application is incorporated herein in its entirety by reference.

FIELD

The present invention relates to an inspection method and apparatus. The inspection method and apparatus may be used to inspect an imprint lithography template.

BACKGROUND

In lithography, there is an ongoing desire to reduce the size of features in a lithographic pattern in order to increase the density of features on a given substrate area. In photolithography, the push for smaller features has resulted in the development of technologies such as immersion lithography and extreme ultraviolet (EUV) lithography, which are however rather costly.

A potentially less costly road to smaller features (e.g., nanometer sized feature or sub micron sized features) that has gained increasing interest is so-called imprint lithography, which generally involves the use of a "stamp" (often referred to as an imprint template or an imprint lithography template) to transfer a pattern onto a substrate. An advantage of imprint lithography is that the resolution of the features is not limited by, for example, the emission wavelength of a radiation source or the numerical aperture of a projection system. Instead, the resolution is mainly limited to the pattern density on the imprint lithography template.

Imprint lithography involves the patterning of an imprintable medium on a surface of a substrate to be patterned. The patterning may involve bringing together a patterned surface of an imprint lithography template and a layer of imprintable liquid medium (e.g., moving the imprint lithography template toward the imprintable medium, or moving the imprintable medium toward the imprint lithography template, or both) such that the imprintable medium flows into recesses in the patterned surface and is pushed aside by protrusions on the patterned surface. The recesses define pattern features of the patterned surface of the imprint lithography template. Typically, the imprintable medium is flowable when the patterned surface and the imprintable medium are brought together. Following patterning of the imprintable medium, the imprintable medium is suitably brought into a non-flowable or frozen state (i.e. a fixed state), for example by illuminating the imprintable medium with actinic radiation. The patterned surface of the imprint lithography template and the patterned imprintable medium are then separated. The substrate and patterned imprintable medium are then typically processed further in order to pattern or further pattern the substrate. The imprintable medium may be provided in the form of droplets on the surface of a substrate to be patterned, but may alternatively be provided using spin coating or the like.

SUMMARY

During use of an imprint lithography template, the imprint lithography template may accumulate defects. For example, the defects may be particles of imprintable medium (e.g. photoresist) that have become deposited on the imprint lithography template during an imprint process. If such defects are not removed, in a subsequent imprint of the imprint lithography template the defect may be physically transferred onto or into the imprintable medium, or the defect may itself provide a corresponding pattern in the imprintable medium. In either example, the pattern that has imprinted into the imprintable medium may be defective.

In order to obviate or mitigate the problem of defects in the form of imprintable medium accumulating on the imprint lithography template, it is desirable to be able to inspect an imprint lithography template in order to detect the presence (or absence) of such a defect. A defect may be removed once detected. Such inspection could, for example, be undertaken using a scanning electron microscope. However, such an inspection method is slow, and may therefore be undesirable. Another inspection method involves detecting the presence of a defect by detecting radiation scattered by the defect. However, in this method, radiation is also scattered by the pattern features of the imprint lithography template itself (e.g. recesses and protrusions of the imprint lithography template), and this can make it difficult or impossible to be able to accurately and consistently detect scattering from the defect, and thus the presence of the defect.

It is desirable, for example, to provide an inspection method and apparatus that obviates or mitigates at least one problem of the art, whether identified herein or elsewhere, or which provides an alternative to an existing inspection method and apparatus.

According to an aspect, there is provided an inspection method for detecting the presence of imprintable medium (e.g. resist or photoresist) on an imprint lithography template, the method comprising: bringing the imprint lithography template and a marker into contact with each other, the marker being attachable to imprintable medium that may be on the imprint lithography template, the marker being configured to interact with incident radiation when attached to the imprintable medium; directing radiation at the imprint lithography template; and measuring radiation re-directed by the imprint lithography template to attempt to detect the presence of a marker that has attached to the imprintable medium, from the interaction of the marker with the incident radiation, and thus detect the presence of imprintable medium to which the marker is attached.

The imprint lithography template may be contacted with the marker after the imprint lithography template has been imprinted into and released from imprintable medium provided on a substrate.

After bringing the imprint lithography template and the marker into contact with each other, one or more markers not attached to the imprintable medium may be removed from the imprint lithography template (e.g. in a cleaning, rinsing, or washing phase or the like, which may involve the use of a solvent).

The imprintable medium may contain an entity configured to attach to the marker. Alternatively or additionally, the marker may contain an entity configured to attach to the imprintable medium.

Prior to bringing the imprint lithography template and the marker into contact with each other, the imprintable medium may be provided with an entity configured to bond with the marker, or the marker may be provided with an entity configured to bond with the imprintable medium.

The entity may be or comprise a reactive group. The reactive group may be one or more of: a primary amine group ($-NH_2$), a thiol group ($-SH$), a carboxyl group ($-COOH$) or an alcohol group ($-OH$).

The marker may be a dye or pigment.

The marker may be a functionalized dye attachable to one or more of: a primary amine group (—NH$_2$), a thiol group (—SH), a carboxyl group (—COOH) or an alcohol group (—OH).

The marker may be configured to interact with incident radiation when attached to the imprintable medium by one or more of: absorbing a particular wavelength of incident radiation, absorbing a first wavelength of incident radiation and emitting a second, different wavelength of radiation, reflecting a particular wavelength of incident radiation, changing the polarization state of incident radiation, and/or changing an intensity of incident radiation.

Measuring radiation re-directed by the imprint lithography template may comprise one or more of: identifying absence or decrease in intensity of a particular wavelength of radiation, identifying presence or increase in intensity of a particular wavelength of radiation, identifying a change in wavelength of the radiation, identifying an increase or decrease in intensity of the radiation, and/or identifying a change in polarization state of the radiation.

The marker when attached to the imprintable medium (which includes the situation when the marker is in isolation) may be photo-luminescent.

The marker when attached to the imprintable medium (which includes the situation when the marker is in isolation) may be fluorescent.

The marker when attached to the imprintable medium (which includes the situation when the marker is in isolation) may be substantially photo-stable.

According to an aspect, there is provided an inspection apparatus to detect presence of imprintable medium, (e.g. resist or photoresist) on an imprint lithography template, the apparatus comprising: a contacting arrangement configured to bring the imprint lithography template and a marker into contact with each other, the marker being attachable to imprintable medium that may be on the imprint lithography template, the marker being configured to interact with incident radiation when attached to the imprintable medium; a radiation arrangement configured to direct radiation at the imprint lithography template; and a measurement arrangement configured to measure radiation re-directed by the imprint lithography template to attempt to detect presence of a marker that has attached to the imprintable medium, from the interaction of the marker with the incident radiation, and thus detect the presence of imprintable medium to which the marker is attached.

The measurement arrangement may be arranged to: identify absence or decrease in intensity of a particular wavelength of radiation, and/or identify presence or increase in intensity of a particular wavelength of radiation, and/or identify a change in wavelength of the radiation, and/or identify an increase or decrease in intensity of the radiation, and/or identify a change in polarization state of the radiation.

BRIEF DESCRIPTION OF THE DRAWINGS

Specific embodiments of the invention will be described with reference to the accompanying Figures, in which.

DETAILED DESCRIPTION

Figure 1A:
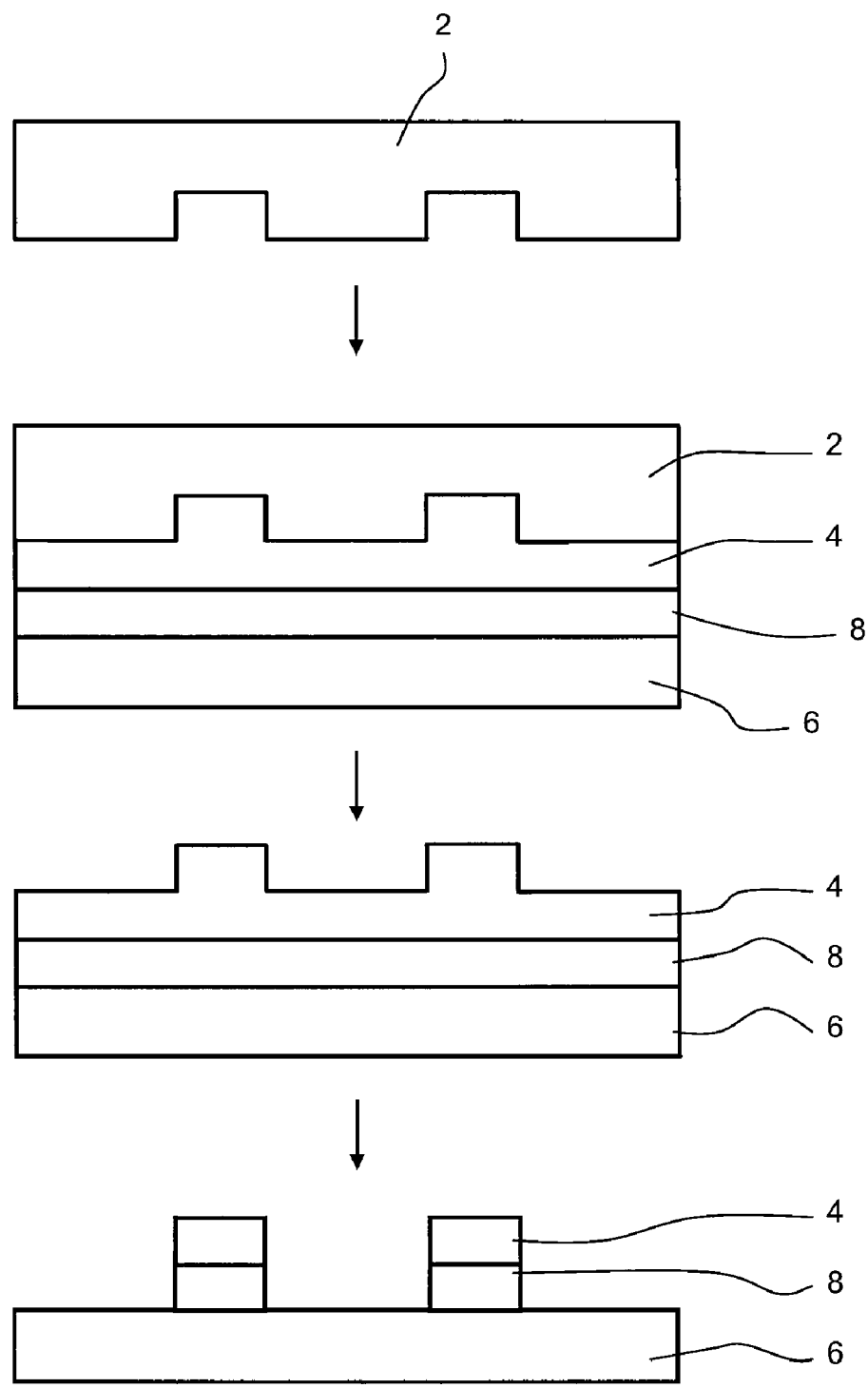
FIGS. 1a and 1b schematically depict examples of, respectively, hot imprint, and UV imprint lithography.
Figure 1B:
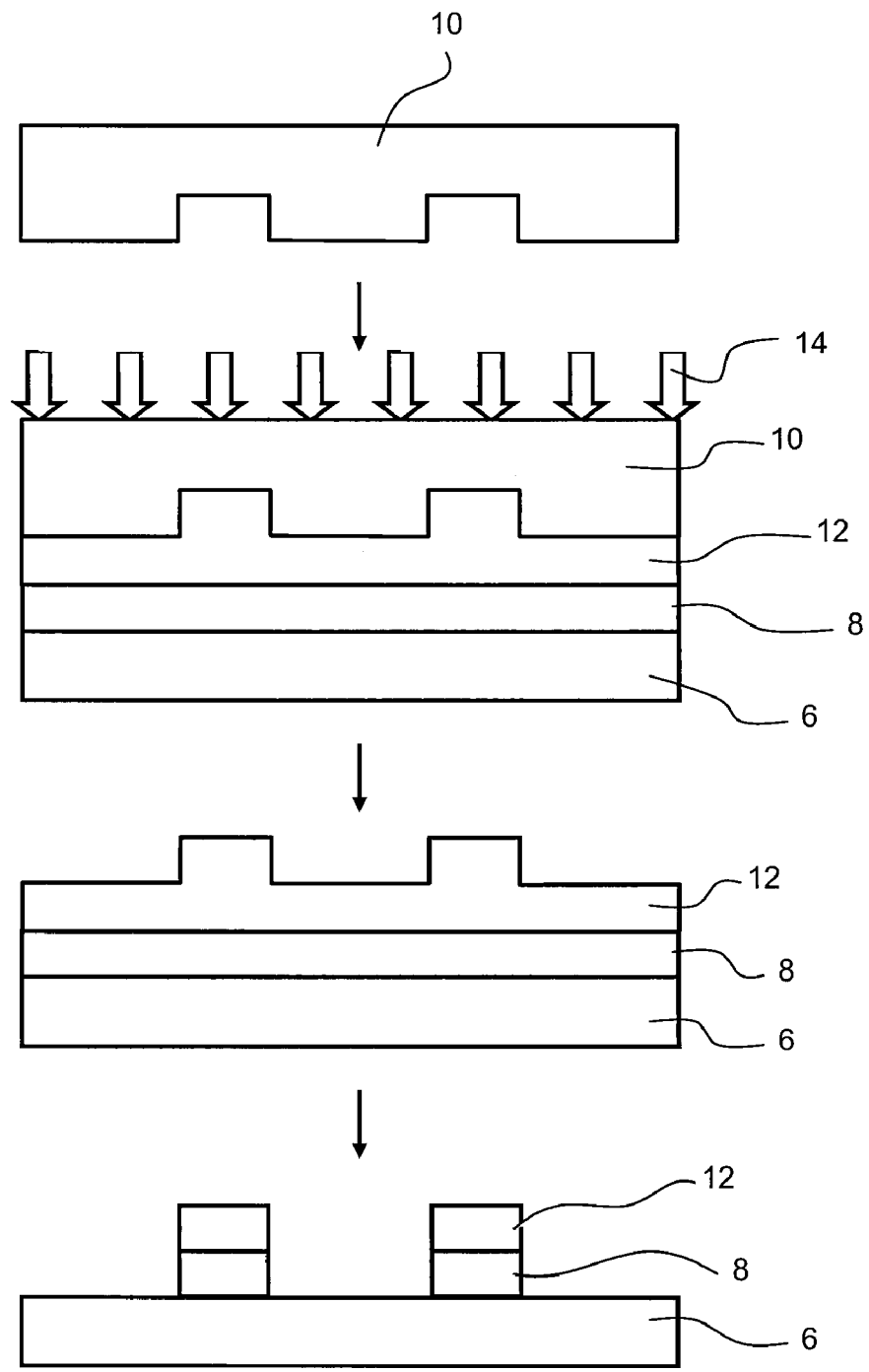

Examples of two known approaches to imprint lithography are schematically depicted in FIGS. 1a to 1b.

FIG. 1a shows an example of so-called hot imprint lithography (or hot embossing). In a typical hot imprint process, an imprint lithography template 2 is imprinted into a thermosetting or a thermoplastic imprintable medium 4, which has been provided on the surface of a substrate 6. The imprintable medium 4 may be, for example, resin. The resin 4 may, for instance, be spin coated and baked onto the substrate surface or, as in the example illustrated, onto a planarization and transfer layer 8 of the substrate 6. When a thermosetting polymer resin 4 is used, the resin 4 is heated to a temperature such that, upon contact with the imprint lithography template 2, the resin 4 is sufficiently flowable to flow into the pattern features defined on the imprint lithography template 2. The temperature of the resin 4 is then increased to thermally cure (crosslink) the resin 4 so that it solidifies and irreversibly adopts the desired pattern. The imprint lithography template 2 may then be removed and the patterned resin 4 cooled. In hot imprint lithography employing a layer of thermoplastic polymer resin, the thermoplastic resin is heated so that it is in a freely flowable state immediately prior to imprinting with the imprint lithography template. It may be necessary to heat thermoplastic resin to a temperature considerably above the glass transition temperature of the resin. The imprint lithography template and flowable resin are brought together and then cooled to below its glass transition temperature with the imprint lithography template in place to harden the pattern. Thereafter, the template is removed. The pattern will consist of the features in relief from a residual layer of the imprintable medium which may then be removed by an appropriate etch process to leave only the pattern features. Examples of thermoplastic polymer resins used in hot imprint lithography processes are poly(methyl methacrylate), polystyrene, poly (benzyl methacrylate) or poly(cyclohexyl methacrylate). For more information on hot imprint, see e.g. U.S. Pat. No. 4,731, 155 and U.S. Pat. No. 5,772,905.

FIG. 1b shows an example of UV imprint lithography, which involves the use of a transparent or translucent imprint lithography template 10 which is transmissive to UV radiation and a UV-curable liquid as imprintable medium 12 (the term "UV" is used here for convenience but should be interpreted as including any suitable actinic radiation for curing the imprintable medium). A UV curable liquid is often less viscous than the thermosetting or thermoplastic resin used in hot imprint lithography and consequently may move much faster to fill imprint lithography template pattern features. A quartz imprint lithography template 10 is applied to a UV-curable resin 12 in a similar manner to the process of FIG. 1a. However, instead of using heat or temperature cycling as in hot imprint lithography, the pattern is frozen by curing the imprintable medium 12 with UV radiation 14 that is applied through the quartz imprint lithography template 10 onto the imprintable medium 12. After removal of the imprint lithography template 10, the imprintable medium 12 is etched (and/or undergoes other further processing) to, for example provide pattern features in the substrate 6. A particular manner of patterning a substrate through UV imprint lithography is so-called step and flash imprint lithography (SFIL), which may be used to pattern a substrate in small steps in a similar manner to optical steppers conventionally used in IC manufacture. For more information on UV imprint, see e.g. U.S. Patent Application Publication No. 2004-0124566, U.S. Pat. No. 6,334,960, PCT Patent Application Publication No. WO 02/067055, and the article by J. Haisma entitled "Mold-assisted nanolithography: A process for reliable pattern replication", J. Vac. Sci. Technol. B14(6), November/December 1996.

Combinations of the above imprint techniques are also possible. See, e.g., U.S. Patent Application Publication No. 2005-0274693, which mentions a combination of heating and UV curing an imprintable medium.

During use, an imprint lithography template may accumulate defects such as particles of imprintable medium (e.g. photoresist or resist), or other contamination. If not detected and removed prior to or during subsequent imprints of the imprint lithography template, the defect may be physically transferred to the imprintable medium, or the defect may provide a pattern feature in the imprintable medium. In either example, the imprinted pattern may be defective. It is therefore desirable to be able to inspect the imprint lithography template in order to detect the presence of a defect, and subsequently remove that defect.

Figure 2:
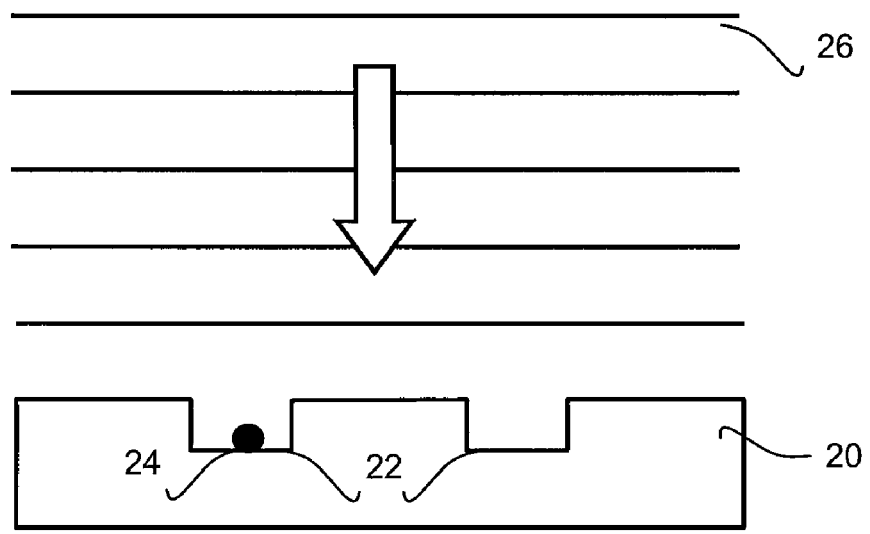
FIG. 2 schematically depicts principles associated with an inspection method.

An example inspection method for detecting the presence of a defect on an imprint lithography template is shown in FIG. 2. FIG. 2 schematically depicts an imprint lithography template 20 (for example, the imprint lithography template shown in and described with reference to FIGS. 1a and/or 1b). Recesses 22 in the imprint lithography template 20 provide pattern features which may be used to provide a pattern in imprintable medium. Located in a recess 22 of the imprint lithography template 20 is a defect 24 in the form of a particle. For example, the particle may be or comprise imprintable medium in the form of photoresist.

The inspection method comprises directing radiation 26 at the imprint lithography template 20. The radiation 26 may be directed at a specific local area or a large area (e.g. a majority or all of the area) of the imprint lithography template 20 at any one time. Alternatively or additionally, there may be relative movement between radiation 26 (or a source of the radiation) and the imprint lithography template 20 to inspect a part of or the entire imprint lithography template 20.

Figure 3:
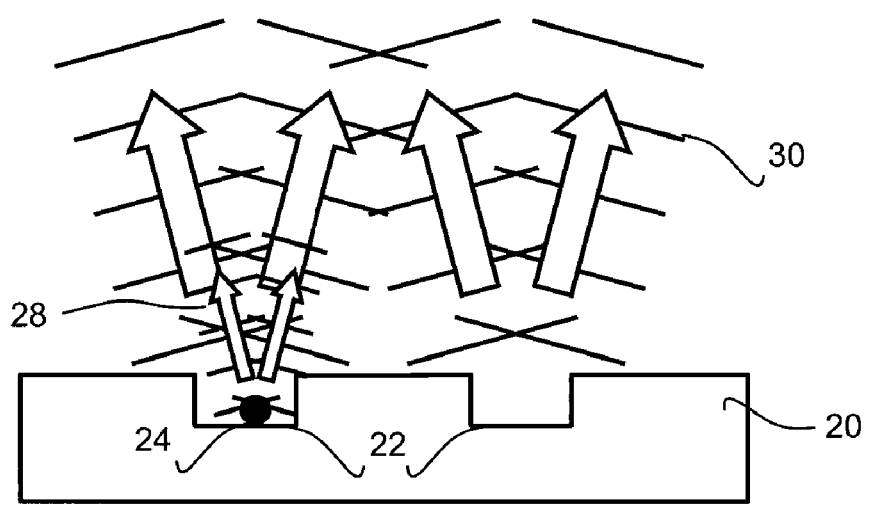
FIG. 3 schematically depicts further principles associated with the inspection method of FIG. 2.

FIG. 3 shows that radiation is re-directed (i.e. scattered, in this embodiment) by the imprint lithography template 20 and the defect 24. Specifically, a small portion of radiation 28 is scattered by the defect 24. A much larger portion of radiation 30 is scattered by pattern features (e.g. recesses 22 and protrusions formed by the provision of those recesses 22) of the imprint lithography template 20. The scattering of the much larger portion of radiation 30 makes it difficult or impossible to be able to accurately and consistently detect the smaller portion of radiation 28 scattered by the defect 24. Because this smaller portion of radiation 28 is difficult or impossible to detect, the presence of the defect 24 can also be difficult or impossible to detect.

In order to be able to detect the defect 24, it is desirable to be able to provide an improved inspection method which does not rely on scattering (or solely on scattering) of radiation by the defect 24.

According to an embodiment of the present invention, there is provided an inspection method for detecting the presence of imprintable medium (e.g. resist or photoresist) on an imprint lithography template. The method comprises bringing the imprint lithography template and a marker into contact with each other. The marker is attachable to imprintable medium that may be on the imprint lithography template. The marker is configured to interact with incident radiation when attached to the imprintable medium. The marker may interact with incident radiation in isolation, or only interact with incident radiation when attached to the imprintable medium. The method further comprises directing radiation at the imprint lithography template (and thus the marker, if applicable). Radiation re-directed by the imprint lithography template is then measured to attempt to detect the presence of a marker that has attached to the imprintable medium. An attempt is made to detect the presence of the marker using the (possible, if the marker is present) interaction of the marker with the incident radiation. The interaction may be such that the intensity-wavelength distribution of re-directed radiation is different from the intensity-wavelength distribution of incident radiation. Detection of the presence of the marker thus results in the detection of the presence of the imprintable medium, since the marker is attached to the imprintable medium.

An embodiment of the invention is advantageous for, for example, a number of reasons. For instance, the method does not need to rely on scattering (or solely on scattering) of radiation in order to detect the imprintable medium, and therefore does not have one or more disadvantages associated with the use of scattering as a method of detection, as discussed above. Furthermore, since the use of a marker attached to the imprintable medium is used to determine the presence of the imprintable medium, the location of the marker will correspond substantially exactly with the location of the imprintable medium that is attached to the imprint lithography template, meaning that the number, distribution, location or the like of imprintable medium particles, flakes or defects (or the like) on the imprint lithography template can be accurately and readily determined.

An embodiment of the present invention will now be described, by way of example only, with reference to FIGS. 4 to 10. In those Figures, the same features appearing in different Figures have been given the same reference numerals for clarity and consistency. Furthermore, the Figures are not necessarily drawn to any accurate scale.

Figure 4:
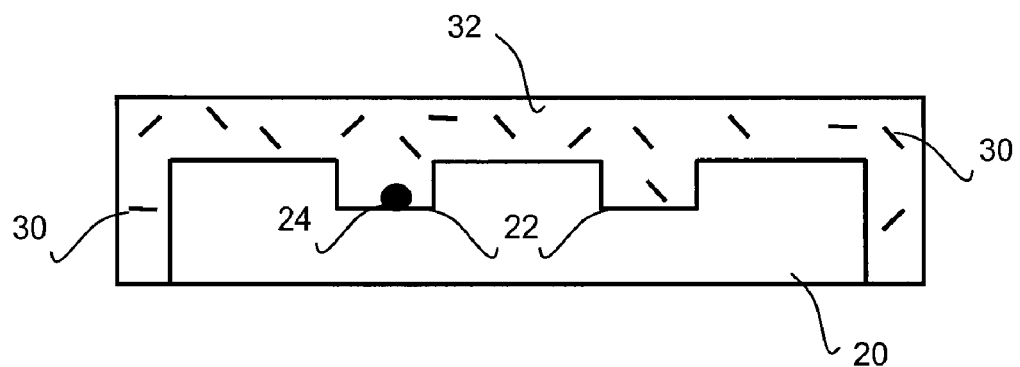
FIG. 4 schematically depicts principles associated with a part of an inspection method according to an embodiment of the present invention.

FIG. 4 schematically depicts the imprint lithography template 20 shown in and described with reference to FIGS. 2 and 3. Specifically, FIG. 4 schematically depicts the imprint lithography template 20 provided with recesses 22. The recesses 22 or protrusions formed around the recesses 22 provide pattern features which may be used to provide a pattern in imprintable medium (e.g. photoresist).

Located in a recess 22 of the imprint lithography template 20 is a defect 24 in the form of a particle, flake, or the like of photoresist 24 (in another embodiment, not shown, the defect may be a particle, flake, or the like of any type of imprintable medium). The photoresist 24 may have become deposited on the imprint lithography template 20 during an imprint step or imprint process or the like, in which the imprint lithography template 20 is imprinted into imprintable medium comprising partially or entirely of photoresist.

After the imprint lithography template 20 has been imprinted into and released from photoresist provided on a substrate or the like, the imprint lithography template 20 is contacted with a marker 30. The marker 30 may be provided in any suitable form, and may for example be in solution or suspension in a body of fluid 32 or the like. The marker 30 may be contacted with the imprint lithography template 20 in any of a number of ways. For example, the marker 30 may be contacted with the imprint lithography template 20 by spraying the marker 30 (or a fluid containing the marker 30) onto the imprint lithography template. Alternatively, and as illustrated in FIG. 4, the marker 30 may be contacted with the imprint lithography template 20 by immersing at marker or markers 30. In summary, the contact may be made in any way which brings the imprint lithography template 20 and marker 30 into contact with each other.

In another example (not shown), the marker 30 could be added to photoresist before the imprint lithography template 20 was imprinted into that photoresist. Thus, the marker would already be present on or in any photoresist remaining on the imprint lithography template 20 after the imprint had taken place. However, this approach may, at least in some circumstances, be disadvantageous. For instance, the marker 30 may be a dye or the like which may absorb UV radiation. UV radiation is commonly used to cure or freeze in position a pattern provided in photoresist when an imprint lithography template has been imprinted into the photoresist. Because the marker 30 may absorb UV radiation that is used to cure or freeze the pattern in the photoresist, a much higher dose of radiation may be required to freeze or fix the pattern in the photoresist, due to the presence of the absorbing marker (e.g. in the form of a dye or the like). A disadvantage of a higher dose of radiation may be its negative effect on temperature stability in the apparatus (e.g. larger temperature variations in an imprint lithography template and/or substrate), which can lead to overlay problems. A further disadvantage is that photoresists are often apolar and can therefore not dissolve polar photostable dyes (e.g. rhodamine dyes, fluorescein dyes or alexa dyes (e.g., sulfonated coumarin, rhodamine, xanthene (such as fluorescein), or cyanine dyes)). Also a curing or fixing process (e.g. involving the use of UV radiation) may bleach or chemically alter the dye such that it becomes non-absorbing or non-luminescent, therefore making the presence of the dye difficult to detect.

Thus, in accordance with an embodiment of the present invention, by bringing the imprint lithography template 20 into contact with the marker after the imprint lithography template has been imprinted into and released from photoresist provided on a substrate (or, in general, after the imprintable medium has become attached to the imprint lithography template), the problems related to absorption are obviated or mitigated. The presence of the marker does not affect the dose of radiation used to cure a pattern provided in the photoresist by the imprint lithography template, since the marker will not be present in or on the photoresist in which a pattern has been provided.

Figure 5:
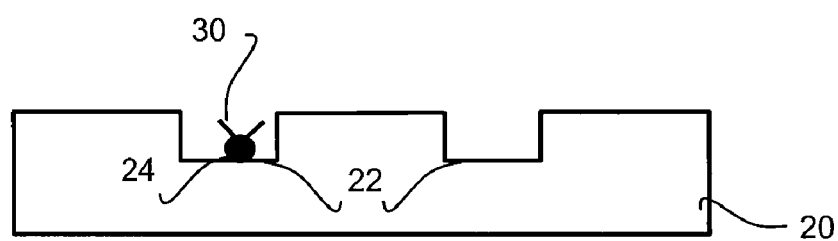
FIG. 5 schematically depicts further principles associated with the inspection method according to an embodiment of the present invention.

FIG. 5 shows that by bringing the imprint lithography template 20 and the marker or markers 30 into contact with each other, one or more markers 30 have become attached to the photoresist 24 that was present on the imprint lithography template 20.

Marker or markers 30 that has not been or become attached to the photoresist can be removed from the imprint lithography template in a cleaning process or the like. Such unattached marker or markers can be removed, for example, by rinsing, or dipping or washing the imprint lithography template in a solvent or the like. The solvent may be a same or similar solvent into which the marker was initially dissolved to be brought into contact with the imprint lithography template. A drying step process may be introduced after the removal of the unattached marker or markers.

The marker or markers 30 are configured to interact with incident radiation when attached to the photoresist. The marker or markers 30 may interact with the incident radiation in isolation, or may only interact with the incident radiation when attached to the photoresist. The interaction may be such that the intensity-wavelength distribution of re-directed radiation is different from the intensity-wavelength distribution of incident radiation. The interaction may take one or more of a number of forms. For example, the interaction may be or comprise: absorbing a particular wavelength of incident radiation, absorbing a first wavelength of incident radiation and emitting a second different wavelength of radiation, reflecting a particular wavelength of incident radiation, changing the polarization state of incident radiation, and/or changing an intensity of incident radiation (in comparison with subsequently re-directed radiation). The marker may be configured to interact in this way by being, for example, photo-luminescent, or fluorescent. Alternatively, or additionally, the marker may preferentially absorb (incident) radiation at certain wavelengths. Typical examples of such markers may be a dye, or a pigment.

All of the described forms of interaction can be readily measured and quantitatively or qualitatively assessed by measuring radiation re-directed by the imprint lithography template (and thus, if present, radiation re-directed by the marker or markers). Such measurement may, for example, take one or more of the following forms: identifying absence or decrease in intensity of a particular wavelength of radiation, identifying presence or increase in intensity of a particular wavelength of radiation, identifying a change in wavelength of the radiation, identifying an increase or decrease in intensity of the radiation, and/or identifying a change in polarization state of the radiation. The measurement may be undertaken in relation to, and/or in comparison with information at least related to the incident radiation (e.g. the intensity-wavelength distribution of the radiation), in order to be able to identify such change, increase, decrease, absence, presence, or the like, of intensity, wavelength or polarization state of the radiation, as discussed above.

Figure 6:
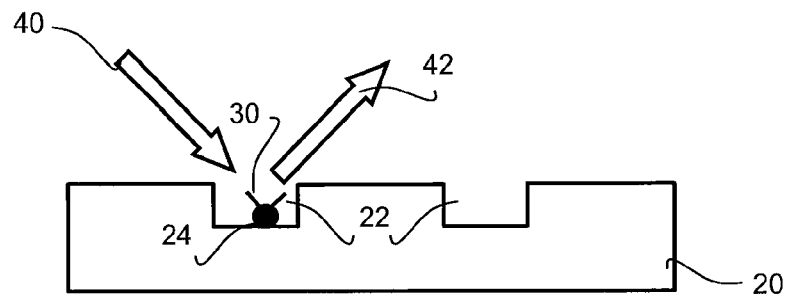
FIG. 6 schematically depicts yet further principles associated with the inspection method according to an embodiment of the present invention.

FIG. 6 schematically depicts the directing of radiation 40 at the imprint lithography template 20. Also depicted is re-directed radiation 42 which may be measured, for example, to attempt to detect or identify presence of marker or markers 30 that has attached to the photoresist 24.

Radiation 40 may be directed at the imprint lithography template 20 in a localized manner, such that a localized beam or the like is scanned relative to the imprint lithography template 20 to attempt to detect the presence of one or more markers 30 on the imprint lithography template 20. Alternatively or additionally, larger areas of the imprint lithography template 20, for example a majority or all of areas of imprint lithography template 20 (e.g. those areas which contribute to patterning), may be irradiated with incident radiation 40. A more localized directing of radiation 40 may provide the ability to more accurately determine the location and amount of photoresist 24 on the imprint lithography template 20, but may take more time than irradiating larger areas of the imprint lithography template 20. Conversely, irradiating larger areas of imprint lithography template 20 may result in a coarser but quicker detection or identification of the presence of photoresist 24 on the imprint lithography template 20.

FIGS. 7 to 10 schematically depict how the presence of a marker, and thus the presence of photoresist, may be detected by directing radiation at the imprint lithography template.

Figure 7:
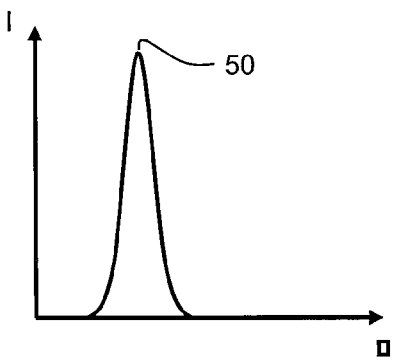
FIGS. 7 to 10 are example graphs schematically depicting intensity-wavelength distributions of radiation directed towards an imprint lithography template, and measurements of radiation re-directed by that imprint lithography template.

FIG. 7 is an example graph depicting an intensity I and wavelength $\lambda$ distribution for incident radiation 50. It can be seen that the incident radiation 50 has a relatively narrow bandwidth centered on a first wavelength. The radiation 50 is directed at the imprint lithography template.

Figure 8:
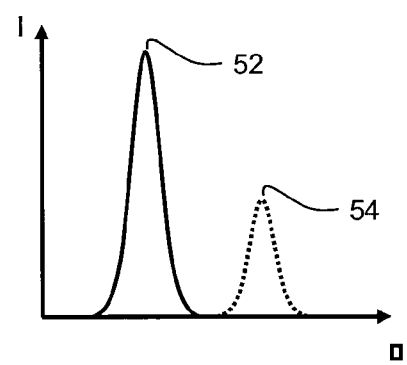

FIG. 8 is a graph depicting the intensity I and wavelength λ distribution of measured radiation that has been re-directed by the imprint lithography template (and thus marker or markers). The measured re-directed radiation may comprise two components: a first radiation component 52 which has a wavelength which corresponds to the wavelength of incident radiation, and a second component 54 which has a wavelength longer than that of the incident radiation. The second component 54 may have a longer wavelength due to, for example, the presence of a fluorescent or photo-luminescent marker that has absorbed photons constituting the incident radiation and has re-emitted photons of a lesser energy and thus longer wavelength. Thus, the presence of the second component 54 is indicative of the presence of a marker and thus photoresist on the imprint lithography template to which the marker is attached.

The marker(s) and/or the wavelength(s) of the incident radiation 50 will be chosen to cause photoluminescence or fluorescence of or in the marker.

Figure 9:
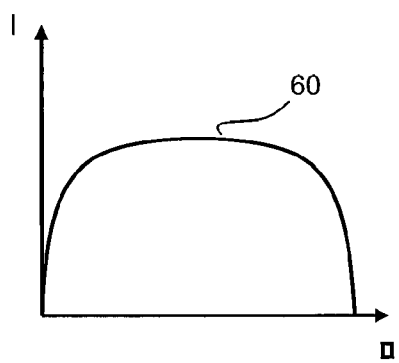

FIG. 9 is a graph schematically depicting another intensity I and wavelength λ distribution of incident radiation 60. The incident radiation 60 has a broad bandwidth. The radiation 60 is directed at the imprint lithography template.

Figure 10:
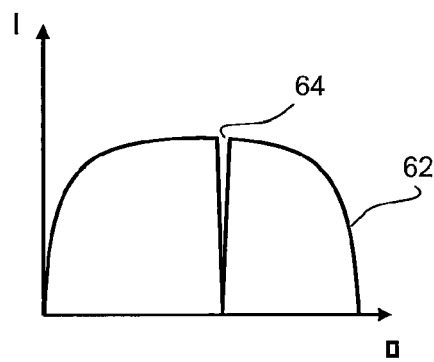

FIG. 10 is a graph depicting an intensity I and wavelength λ distribution of radiation re-directed by the imprint lithography template, which includes any markers located thereon. The re-directed radiation 62 again has a broad bandwidth. A marker on the imprint lithography template may be configured to absorb radiation at a particular wavelength in the broad distribution of radiation constituting the incident radiation. This may result in a notch or gap 64 or the like in the distribution in the re-directed radiation 62. Thus, the presence of the notch or gap 64 indicates the presence of one or more markers, and thus photoresist to which the marker or markers are attached.

The marker(s) and/or the wavelength(s) of the incident radiation 60 will be chosen to cause absorption by the marker.

In general, the marker(s) and/or radiation will be chosen such that the incident radiation comprises of a wavelength or wavelengths which can interact with the marker to effect the distribution of re-directed radiation, which can then be measured to determine the presence of the marker(s), and thus photoresist to which the marker or markers is or are attached. In some embodiments, fluorescence detection may be a more sensitive (and therefore desired) technique than absorption detection.

In order for detection of a marker or markers to be successful, there is not necessarily a need for a large amount or number of marker or markers on any given amount of resist. In fact, single molecule (e.g. single marker) detection has been reported (see e.g. Shimon Weiss, Science 283, 1999, p 1676).

A photoresist may have one or more inherent properties which will result in the marker attaching itself to the photoresist. Alternatively, the photoresist may contain (e.g. be provided with) an entity configured to attach to the marker. The attachment may be a bond or the like, such as for example a chemical bond. Alternatively or additionally, an existing photoresist may be provided with an entity configured to bond with the marker.

The entity may be a reactive group or the like. The reactive group may be one or more of a primary amine group (—NH$_2$), a thiol group (—SH), a carboxyl group (—COOH) or an alcohol group (—OH).

The marker may be a dye or pigment. For instance, the marker may be a functionalized dye attachable to one or more of a primary amine group (—NH$_2$), a thiol group (—SH), a carboxyl group (—COOH) or an alcohol group (—OH).

Dyes (e.g. rhodamine based dyes, fluorescein based dyes, cyanine type dyes or alexa type dyes (e.g., sulfonated coumarin, rhodamine, xanthene (such as fluorescein), or cyanine dyes)) can be functionalized with the above mentioned reactive groups, e.g. in the case of a primary amine group (—NH$_2$) such as: isothiocyanate, succinimidyl ester, tetrafluorophenyl ester, sulfodichlorophenol, sulfonyl chloride, and/or aldehyde, and/or in the case of a thiol group (—SH) such as alkyl halide, haloacetemide, and/or maleimide. Linkage of amine groups with carboxyl groups can occur with the assistance of carbodiimides. For alcohols there may be a specific dye that can be used (e.g. N-methylisatoic anhydride, which is fluorescent in contact with alcohols).

Other markers may be used, such as for example one or more nanoparticles, quantum dots, nano-phosphors, metal-containing dyes or the like. A (e.g. metal free) dye or pigment may be desirable, however, since such a dye or pigment may be easily removed from the imprint lithography template during a cleaning stage or the like undertaken when photoresist is found to be present on the imprint lithography template (or at any other stage). Whatever marker is used is desirably photo-stable so that the irradiation of the marker does not adversely affect the ability of the marker to interact with radiation and thus reveal the presence of photoresist to which the marker is attached. Typical photo-stable dyes are rhodamine based dyes, fluoresceine based dyes, cyanine type dyes and alexa type dyes.

According to an embodiment of the present invention, there is provided an inspection apparatus to undertake the method described above. The inspection apparatus is suitable to detect the presence of imprintable medium on an imprint lithography template.

The apparatus may comprise a contacting arrangement configured to bring the imprint lithography template and a marker into contact with each other. The contacting arrangement may take one of a number of different forms. For example, the contacting arrangement may comprise a bath or other reservoir containing the marker, or a fluid containing that marker, and one or more actuators to bring the imprint lithography template and the marker into contact with one another (e.g. to immerse at least a part of the imprint lithography template in the fluid containing the marker). In another example, the contacting arrangement could be a nozzle and/or dispenser which is used to direct a fluid or the like containing or constituting the marker onto the imprint lithography template (e.g. in the form of a spray or the like).

The apparatus may further comprise a radiation arrangement configured to direct radiation at the imprint lithography template. The radiation arrangement may comprise a radiation source. Alternatively or additionally, the radiation arrangement may comprise one or more lenses, reflectors, filters or the like. The radiation source may be tunable to be able to tune the wavelength or wavelengths emitted by the radiation source.

In the method described above, radiation is directed at the imprint lithography template. This may not be radiation specifically generated solely for the purpose of or for directing radiation at the imprint lithography template. For instance, in an example the radiation may be ambient radiation. For instance, ambient radiation may be incident on the imprint lithography template, and cause photoluminescence or fluorescence in or of the markers, which is detectable by a measurement arrangement or the like. Thus, the radiation arrangement may not be a dedicated laser or other radiation source or the like, but may simply be background ambient lighting or the like.

The apparatus may further comprise a measurement arrangement configured to measure radiation re-directed by the imprint lithography template. Such measurement is undertaken to attempt to detect the presence of a marker that has attached to the imprintable medium, from the interaction of the marker with the incident radiation, and thus detect the presence of imprintable medium to which the marker is attached. The measurement arrangement may be arranged to: identify absence or decrease in intensity of a particular wavelength of radiation; and/or identify presence or increase in intensity of a particular wavelength of radiation; and/or identify a change in wavelength of the radiation; and/or identify an increase or decrease in intensity of the radiation; and/or identify a change in polarization state of the radiation. The measurement arrangement may, for example, comprise a detector (e.g. photo-diode, CCD camera, or the like) or the like which may be in connection with a computational device or comparator to, for example, compare the measured re-directed radiation with information at least representative of the incident radiation. The measurement arrangement may be in wired or wireless connection with the radiation arrangement to be able to undertake such comparisons.

In any embodiment, once imprintable medium has been detected on the imprint lithography template, further action may be taken. For example, the imprint lithography template may be exchanged for a clean (imprintable medium free) imprint lithography template. Alternatively or additionally, the imprint lithography template may be cleaned. Cleaning of the imprint lithography template may be undertaken in a conventional manner, for example using one or more fluids or the like. Such cleaning will desirably remove any marker on the imprint lithography template.

In the embodiments described above, photoresist has been described as being attached the imprint lithography template. Markers are described as being attachable or attached to the photoresist. The material attached to the imprint lithography template, and to which the marker or markers are attachable may be a material other than photoresist. For example, the material may be a resist that is curable by heating, and not by irradiation with UV radiation. In another example, the material may be a material which can be embossed using an imprint lithography template. In summary, the material may be any imprintable medium, for example a medium in which a pattern may be formed by imprinting an imprint lithography template into that imprintable medium.

Features of one or more of the above described embodiments of the invention may be combined together.

The present invention relates to imprint lithography apparatus and methods. The apparatus and/or methods may be used for the manufacture of devices, such as electronic devices and integrated circuits or other applications, such as the manufacture of integrated optical systems, guidance and detection patterns for magnetic domain memories, flat-panel displays, liquid-crystal displays (LCDs), thin film magnetic heads, organic light emitting diodes, etc.

In this specification, the term "substrate" is meant to include any surface layers forming part of the substrate, or being provided on another substrate, such as planarization layers or anti-reflection coating layers.

In the above embodiments, a single imprint template, a single imprint template holder, a single substrate holder and a single substrate is provided in a single chamber. In other embodiments, more than one imprint template, more than one imprint template holder, more than one substrate holder, and/or more than one substrate may be provided in one or more chambers, in order for imprints to be undertaken more efficiently or quickly (e.g. in parallel). For example, in an embodiment, there is provided an apparatus that includes a plurality (e.g. 2, 3, or 4) of substrate holders. In an embodiment, there is provided an apparatus that includes a plurality (e.g. 2, 3, or 4) of imprint template arrangements. In an embodiment, there is provided an apparatus configured to use one template holder arrangement per substrate holder. In an embodiment, there is provided an apparatus configured to use more than one template holder arrangement per substrate holder. In an embodiment, there is provided an apparatus that includes a plurality (e.g. 2, 3, or 4) of imprintable medium dispensers. In an embodiment, there is provided an apparatus configured to use one imprintable medium dispenser per substrate holder. In an embodiment, there is provided an apparatus configured to use one imprintable medium dispenser per imprint template arrangement. In an embodiment, where an apparatus is provided that includes a plurality of substrate holders, the substrate holders may share functionalities in the apparatus. For instance, the substrate holders may share a substrate handler, a substrate cassette, a gas supply system, an imprintable medium dispenser, and/or a radiation source (for curing the imprintable medium). In an embodiment, two or more of the substrate holders (e.g. 3 or 4) share one or more functionalities of the apparatus (e.g. 1, 2, 3, 4, or 5 functionalities). In an embodiment, one or more functionalities (e.g. 1, 2, 3, 4, or 5) of the apparatus are shared among all substrate holders.

The described and illustrated embodiments are to be considered as illustrative and not restrictive in character, it being understood that only embodiments have been shown and described and that all changes and modifications that come within the scope of the invention as defined in the claims are desired to be protected. It should be understood that while the use of words such as "preferable", "preferably", "preferred" or "more preferred" in the description suggest that a feature so described may be desirable, it may nevertheless not be necessary and embodiments lacking such a feature may be contemplated as within the scope of the invention as defined in the appended claims. In relation to the claims, it is intended that when words such as "a," "an," "at least one," or "at least one portion" are used to preface a feature there is no intention to limit the claim to only one such feature unless specifically stated to the contrary in the claim. When the language "at least a portion" and/or "a portion" is used the item can include a portion and/or the entire item unless specifically stated to the contrary.

The invention claimed is:

1. An inspection method for detecting the presence of imprintable medium on an imprint lithography template, the method comprising:
   bringing the imprint lithography template and a marker into contact with each other, the marker being attachable to imprintable medium that may be on the imprint lithography template, the marker being configured to interact with incident radiation when attached to the imprintable medium;
   directing radiation at the imprint lithography template; and
   measuring radiation re-directed by the imprint lithography template to attempt to detect the presence of a marker that has attached to the imprintable medium, from the interaction of the marker with the incident radiation, and thus detect the presence of imprintable medium to which the marker is attached.

2. The inspection method of claim 1, wherein the imprint lithography template is contacted with the marker after the imprint lithography template has been imprinted into and released from imprintable medium provided on a substrate.

3. The inspection method of claim 1, wherein, after bringing the imprint lithography template and the marker into contact with each other, one or more markers not attached to the imprintable medium are removed from the imprint lithography template.

4. The inspection method of claim 1, wherein the imprintable medium contains an entity configured to attach to the marker.

5. The inspection method of claim 4, wherein the entity is a reactive group.

6. The inspection method of claim 5, wherein the reactive group is one or more of: a primary amine group (—$NH_2$), a thiol group (—SH), a carboxyl group (—COOH) or an alcohol group (—OH).

7. The inspection method of claim 1, wherein the marker is a dye or pigment.

8. The inspection method of claim 1, wherein the marker is a functionalized dye attachable to one or more of: a primary amine group (—$NH_2$), a thiol group (—SH), a carboxyl group (—COOH) or an alcohol group (—OH).

9. The inspection method of claim 1, wherein the marker is configured to interact with incident radiation when attached to the imprintable medium by one or more of: absorbing a particular wavelength of incident radiation, absorbing a first wavelength of incident radiation and emitting a second, different wavelength of radiation, reflecting a particular wavelength of incident radiation, changing the polarization state of incident radiation, and/or changing an intensity of incident radiation.

10. The inspection method of claim 1, wherein measuring radiation re-directed by the imprint lithography template comprises one or more of: identifying absence or decrease in intensity of a particular wavelength of radiation, identifying presence or increase in intensity of a particular wavelength of radiation, identifying a change in wavelength of the radiation, identifying an increase or decrease in intensity of the radiation, and/or identifying a change in polarization state of the radiation.

11. The inspection method of claim 1, wherein the marker when attached to the imprintable medium is photo-luminescent.

12. The inspection method of claim 1, wherein the marker when attached to the imprintable medium is fluorescent.

13. The inspection method of claim 1, wherein the marker when attached to the imprintable medium is substantially photo-stable.

14. An inspection apparatus to detect presence of imprintable medium, the apparatus comprising:
an imprint lithography template;
a contacting arrangement configured to bring the imprint lithography template and a marker into contact with each other, the marker being attachable to imprintable medium that may be on the imprint lithography template, the marker being configured to interact with incident radiation when attached to the imprintable medium;
a radiation arrangement configured to direct radiation at the imprint lithography template; and
a measurement arrangement configured to measure radiation re-directed by the imprint lithography template to attempt to detect presence of a marker that has attached to the imprintable medium, from the interaction of the marker with the incident radiation, and thus detect the presence of imprintable medium to which the marker is attached.

15. The inspection apparatus of claim 14, wherein the measurement arrangement is arranged to: identify absence or decrease in intensity of a particular wavelength of radiation, and/or identify presence or increase in intensity of a particular wavelength of radiation, and/or identify a change in wavelength of the radiation, and/or identify an increase or decrease in intensity of the radiation, and/or identify a change in polarization state of the radiation.

16. The inspection apparatus of claim 14, configured to, after bringing the imprint lithography template and the marker into contact with each other, remove one or more markers not attached to the imprintable medium from the imprint lithography template.

17. The inspection apparatus of claim 14, wherein the marker is configured to interact with incident radiation when attached to the imprintable medium by one or more of: absorbing a particular wavelength of incident radiation, absorbing a first wavelength of incident radiation and emitting a second, different wavelength of radiation, reflecting a particular wavelength of incident radiation, changing the polarization state of incident radiation, and/or changing an intensity of incident radiation.

18. The inspection apparatus of claim 14, wherein the marker when attached to the imprintable medium is photo-luminescent.

19. The inspection apparatus of claim 14, wherein the marker when attached to the imprintable medium is fluorescent.

20. The inspection apparatus of claim 14, wherein the marker when attached to the imprintable medium is substantially photo-stable.

* * * * *